United States Patent [19]

Ikada et al.

[11] Patent Number: 4,999,110
[45] Date of Patent: Mar. 12, 1991

[54] REGENERATED CELLULOSE MEMBRANE AND PROCESSES FOR PREPARATION THEREOF

[75] Inventors: Yoshito Ikada, Uji; Hikaru Konishi; Eugene Corretge, both of Kyoto; Kazuo Imamura, Nobeoka, all of Japan

[73] Assignee: Asahi Kasei Kogyo Kabushiki Kaisha, Osaka, Japan

[21] Appl. No.: 488,511

[22] Filed: Feb. 28, 1990

Related U.S. Application Data

[63] Continuation of Ser. No. 116,785, Nov. 5, 1987, abandoned.

[30] Foreign Application Priority Data

Nov. 7, 1986 [JP] Japan ................................ 61-266473
Oct. 9, 1987 [JP] Japan ................................ 62-253724

[51] Int. Cl.$^5$ ............................................. B01D 69/00
[52] U.S. Cl. ................................ 210/490; 210/500.24; 210/500.29; 427/245
[58] Field of Search ............. 210/490, 500.24, 500.29, 210/500.30, 500.31; 427/245, 246, 2, 3

[56] References Cited

U.S. PATENT DOCUMENTS

| Re. 32,277 | 11/1986 | Tsuge et al. | 210/500.29 |
|---|---|---|---|
| 3,616,935 | 11/1971 | Love | 210/500 |
| 4,604,326 | 8/1986 | Manabe et al. | 428/398 |
| 4,668,396 | 5/1987 | Baurmeister et al. | 210/500.29 |

FOREIGN PATENT DOCUMENTS

| 155534 | 9/1985 | European Pat. Off. | |
| 334113 | 11/1921 | Fed. Rep. of Germany | |
| 0036388 | 3/1979 | Japan | 210/500.29 |
| 0007206 | 1/1982 | Japan | 210/500.29 |
| 7406498 | 11/1974 | Netherlands | 210/500.29 |

OTHER PUBLICATIONS

Malm et al., Industrial and Engineering Chemistry, pp. 684–688, Mar. 1951.
Malm et al., Industrial and Engineering Chemistry, pp. 688–691, Mar. 1951.
Kirk-Othmer, Encylcopedia of Chemical Technology, 3rd ed., vol. 5, pp. 118–121.
Kirk-Othmer, Encylcopedia of Chemical Technology, 3rd ed., vol. 10, pp. 118–121.

*Primary Examiner*—Frank Spear
*Attorney, Agent, or Firm*—Finnegan, Henderson, Farabow, Garrett & Dunner

[57] ABSTRACT

An improved regenerated cellulose membrane formed by ester-bonding an organic carboxylic acid or a functional derivative thereof to a polymeric membrane composed of a regenerated cellulose. This regenerated cellulose membrane exhibits an improved blood compatibility without lowering the dialysis performances of a regenerated cellulose membrane.

10 Claims, No Drawings

REGENERATED CELLULOSE MEMBRANE AND PROCESSES FOR PREPARATION THEREOF

This application is a continuation of application Ser. No. 07/116,785 filed Nov. 5,1987, now abandoned.

BACKGROUND OF THE INVENTION (1) Field of the Invention

The present invention relates to an improved regenerated cellulose membrane to be used for an artificial organ and the like and a process for the preparation thereof. More particularly, the present invention relates to a regenerated cellulose membrane having an improved blood compatibility, and a process for the preparation thereof.

(2) Description of the Related Art

Recently, rapid progress has been made in the development of artificial organs such as an artificial kidney and an artificial lung, and in a plasma-separating apparatus and as is well-known, especially in hemodialysis therapy, a regenerated cellulose membrane, particularly a cuprammonium regenerated cellulose membrane, is widely used. Together with the development of dialysis apparatuses or dialysis techniques, the regenerated cellulose membrane has made great contributions to the survival and rehabilitation of patients with end-stage renal disease. This importance of the regenerated cellulose membrane is due to the excellent dialysis performance, high mechanical strength, and high safety level thereof obtained in practical use over many years.

Nevertheless, in spite of the progress made in hemodialysis therapy, many problems concerning the dialysis still remain. For example, the problem of a side effect stemming from a long-period administration of a large quantity of an anti-coagulant and as has been pointed out, if hemodialysis using a regenerated cellulose membrane or a certain other kinds membrane is carried out, a transient reduction of leukocytes or activation of the complement occurs. The relationship between the latter phenomena and the clinical symptoms, or the clinical significance, has not been clarified, but there is obviously a need to provide a regenerated cellulose membrane capable of moderating these phenomena without an adverse affect on the excellent dialysis performances of the regenerated cellulose membrane mentioned above.

Membranes composed of synthetic polymers have been proposed to moderate the above problems or phenomena, but these membranes themselves have problems in that they have a poor mechanical strength and is very susceptible to the formation of pinholes, it is difficult to sterilize because of a low heat resistance, and is difficult to apply because the properties thereof are not well-balanced, that is, a good balance cannot be maintained between the amount of water permeability and the amount of substance permeability.

Various methods have been proposed for improving the blood compatibility in regenerated cellulose membranes. For example, U.S. Pat. No. 3,616,935 proposes a method in which the surface of a membrane is modified with heparin to impart an anti-thrombus property to the membrane. However, the effect attained is not satisfactory and the cost is high. Another method has been proposed in which the surface of a regenerated cellulose membrane is coated with a polymer or a vitamin. However, the coating stability is unsatisfactory or sterilization is difficult. European Patent No. 155,534 proposes a method in which a regenerated cellulose membrane is reacted with an isocyanate prepolymer, and DE 334,113 proposes a method in which a polymer acid is chemically bonded to a regenerated cellulose membrane through a bridging agent. These methods, however, are unsatisfactory in that the reactants have a poor stability and the reaction steps are complicated. European Patent No. 172,437 (U.S. Pat. No. 4,668,396) proposes a dialysis membrane formed by using a modified cellulose such as diethylaminoethyl cellulose. However, the improvement in the effect of moderating the coagulation of blood is not satisfactory.

SUMMARY OF THE INVENTION

Therefore, it is a primary object of the present invention to provide an improved regenerated cellulose membrane exhibiting an improved blood compatibility without a lowering of the dialysis performances of a regenerated cellulose membrane, and a process for the preparation of this improved regenerated cellulose membrane.

It is considered that the hydroxyl group on the membrane surface participates in transient reduction of leukocytes or activation of the complement, observed when a regenerated cellulose membrane is used, and that the hydroxyl group on the membrane surface is capable of reacting with various functional groups and bonding molecule chains. The bonded molecule chain masks the hydroxyl group on the membrane to prevent the hydroxyl group from coming into direct contact with a complement protein or blood cell, and accordingly, the activation of the complement is moderated, and the physical and chemical properties of the membrane surface are changed so that the blood compatibility is improved. Many combinations of the structure of the molecule chain and the functional group can be considered. Accordingly, taking into consideration the safety factor, the biocompatibility, the economical advantages, and the chemical reactivity, the present inventors have now completed the present invention.

More specifically, in accordance with one aspect of the present invention, there is provided an improved regenerated cellulose membrane formed by ester-bonding an organic carboxylic acid or a functional derivative thereof to at least a blood-contacting surface of a regenerated cellulose membrane In accordance with another aspect of the present invention, there is provided a process for the preparation of an improved regenerated cellulose membrane, which comprises treating a regenerated cellulose membrane with a liquid prepared by dissolving or dispersing an organic carboxylic acid or a functional derivative thereof and an esterification catalyst in a reaction medium to effect an esterification reaction between the organic carboxylic acid or the functional derivative thereof and the hydroxyl groups on the surface of the membrane.

DESCRIPTION OF THE PREFERRED EMBODIMENTS

By the term "regenerated cellulose" used herein is meant a cellulose obtained by regenerating a chemically or physically modified natural cellulose. For example, there can be mentioned cuprammonium regenerated cellulose, viscose rayon, and saponified cellulose ester. From the viewpoint of dialysis performance and safety, as supported by practical results, a cuprammonium regenerated cellulose is preferably used.

Regarding the shape of the regenerated cellulose, either a flat membrane or a hollow fiber membrane can be used, but a hollow fiber membrane is preferred. For example, a hollow fiber membrane having a wall-thickness of several to 60 μm and a cross-section of a true circle having an outer diameter of 10 to several hundred μm, as disclosed in U.S. Pat. No. 3,888,771 (RE No. 32,277) and U.S. Pat. No. 4,604,326, is preferably used.

By the term "grafted chain" used hereinafter is meant a molecule chain having at least one end chemically bonded to the surface of the membrane, and in the present invention, the grafted chain corresponds to an organic carboxylic acid residue ester-bonded to the surface of the membrane. Accordingly, an organic carboxylic acid or a derivative thereof, capable of forming an ester linkage with the hydroxyl groups on the membrane surface, can be used, and the number of the carboxyl group or the functional derivative group as the functional group is not limited to one, and the organic carboxylic acid may have two or more such functional groups.

As the organic carboxylic acid used in the present invention, there can be mentioned polymeric carboxylic acids, namely high-molecular-weight carboxylic acids having the following repeating unit of the grafted chain

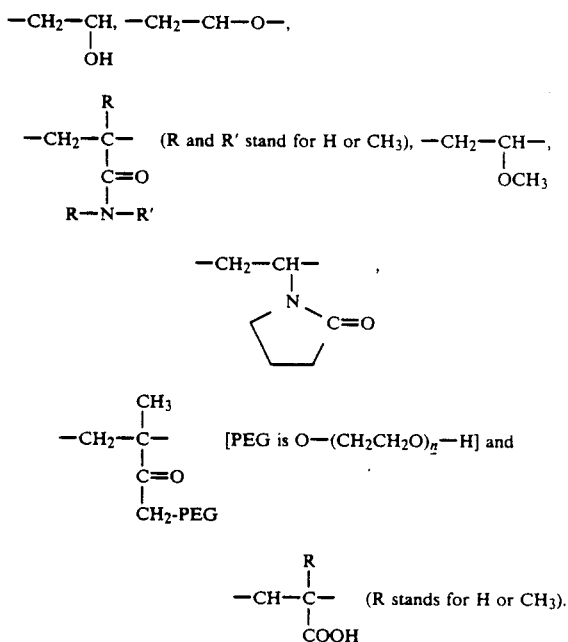

In view of the anti-thrombus property, preferably the last-mentioned carboxyl group-containing repeating unit is contained in only a small amount in the form of a copolymer.

Among these polymeric carboxylic acids preferable are polyethylene glycol dicarboxylic acids represented by the following general formula:

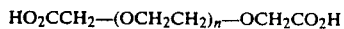

wherein n is an integer of from 1 to 150, and polyethylene glycol monocarboxylic acids represented by the following general formula:

wherein R stands for saturated or unsaturated hydrocarbon group having 1 to 20 carbon atoms and n is an integer of from 1 to 150.

An aliphatic carboxylic acid also can be used as the organic carboxylic acid, and as the aliphatic carboxylic acid, there can be mentioned saturated or unsaturated fatty acids and aliphatic dicarboxylic acids. In view of the effect of masking the hydroxyl group on the membrane, aliphatic carboxylic acids having 5 to 30 carbon atoms are preferred. More specifically, there can be mentioned saturated fatty acids such as valeric acid, caproic acid, enanthic acid, caprylic acid, pelargoni acid, capric acid, undecylic acid, lauric acid, tridecylic acid, myristic acid, pentadecylic acid, palmitic acid, heptadecylic acid, stearic acid, nonadecanoic acid, arachic acid, behenic acid, and lignoceric acid; unsaturated fatty acids such as oleic acid, elaidic acid, cetoleic acid, erucic acid, brassidic acid, sorbic acid, linoleic acid, linolenic acid,and arachidonic acid; and aliphatic dicarboxylic acids such as glutaric acid, adipic acid, pimelic acid, suberic acid azelaic acid,and sebacic acid.

In the above-mentioned saturated fatty acids, if the carbon number is increased, the hydrophilic property of the surface of the improved regenerated cellulose membrane is reduced, and accordingly, saturated fatty acids having 5 to 14 carbon atoms are especially preferred.

As pointed out hereinbefore, the number of the carboxyl group or the derivative thereof as the functional group in the molecule is not limited to one. However, in the case of a polyfunctional organic carboxylic acid, sometimes before the reaction with the hydroxyl groups on the membrane surface, the polymerization of the carboxylic acid occurs due to a reaction of the carboxyl groups with each other, with the result that the esterification reactivity is reduced. Moreover, in the case of the polyfunctional carboxylic acid, there is a possibility of a formation of a loopy molecule chain bonded to the membrane surface at two or more points thereof. As pointed out hereinafter, a molecular chain having one end bonded to the membrane surface is preferred, and accordingly, a monocarboxylic acid is preferably used.

In the present invention, a carboxylic acid as mentioned above, or a functional derivative thereof such as a carboxylic acid halide or a carboxylic acid anhydride, is ester-bonded to the surface of the regenerated cellulose membrane to modify the cellulose membrane. From the viewpoint of an ease of handling and the safety of the residue, a carboxylic acid chloride is preferred as the carboxylic acid halide. A simple (i.e., symmetrical) acid anhydride of the above-mentioned carboxylic acid or a mixed (i.e., asymmetrical) acid anhydride composed of the above-mentioned carboxylic acid and another carboxylic acid can be used as the carboxylic acid anhydride. In the case of the mixed acid anhydride, in order to preferentially ester-bond the intended carboxylic acid, a carboxylic acid having a large steric hindrance, such as isobutyric acid or isovaleric acid, or an alkyl hydrogencarbonate (HOCO$_2$R; R=alkyl group) is preferably used as another acid in the mixed acid anhydride.

The carboxylic acid or the functional derivative thereof is used at a concentration as low as 0.1 to 50 millimole/l, and in view of the nonbonded reactant adhering onto the membrane and from the economical viewpoint, preferably the carboxylic acid or the functional derivative thereof is used at a concentration of 0.5 to 10 millimole/l.

The ester bonding to the surface of the regenerated cellulose membrane is accomplished by an esterification reaction between the carboxyl group or the functional derivative thereof and the hydroxyl groups present on the surface of the membrane. The known reaction between a low-molecular-weight alcohol and a low-molecular-weight carboxylic acid or a functional derivative thereof can be applied to this esterification reaction Regarding the treatment conditions, preferably the treatment temperature is controlled to a low level and the treatment time is shortened, so that adverse influences are not imposed on the physical properties of the regenerated cellulose membrane.

Namely, the esterification treatment is carried out preferably at a temperature of from 5° C. to 120° C., and not exceeding the boiling temperature of the reaction medium, for a period of one minute to 24 hours, and more preferably, at a temperature of from 15° C. to 90° C., and not exceeding the boiling temperature of the reaction medium, for a period of 3 minutes to 180 minutes. These treatment conditions are also advantageous from the economical viewpoint. Preferably, an esterification catalyst is used to promote esterification.

When carboxylic acid is used, a mineral acid such as sulfuric acid or hydrochloric acid, an organic acid such as an aromatic sulfonic acid, a Lewis acid such as boron trifluoride etherate, a carbodiimide derivative such as dicyclohexylcarbodiimide, or a mixed catalyst of a carbodiimide derivative and 4-dimethylaminopyridine and/or 4-pyrrolidinopyridine can be used as the esterification catalyst for promoting the reaction. When acid halide is used, pyridine, dimethylaniline, triethylamine, tetramethylurea or metallic magnesium is used for removing the hydrogen halide formed as a by-product by the reaction, and a mixed catalyst of a hydrogen halide-removing agent as described above with 4-dimethylaminopyridine and/or 4-pyrrolidinopyridine is used for promoting the reaction. When acid anhydride is used, as is well-known, sulfuric acid, p-toluene-sulfonic acid, zinc chloride, sodium acetate, pyridine, 4-dimethylaminopyridine or 4-pyrrolidinopyridine is used as the catalyst for promoting the reaction.

In the present invention, these catalysts can be used singly or in the form of an appropriate mixture of two or more thereof In order to ensure a smooth reaction and to facilitate removal of the catalyst after the reaction, preferably as small as an amount possible of a catalyst soluble in the reaction mixture is used. From this viewpoint, preferably there are adopted a method in which the carboxylic acid is subjected to esterification reaction in the presence of a mixed catalyst of a carbodiimide derivative such as dicyclohexylcarbodiimide with 4-dimethylaminopyridine and/or 4-pyrrolidinopyridine, and a method in which the carboxylic anhydride is subjected to esterification reaction in the presence of 4-dimethylaminopyridine and/or 4-pyrrolidinopyridine. The carbodiimide derivative is useful for removing water formed by the reaction and is converted to a corresponding urea derivative. A precipitate is sometimes formed according to the kind of the reaction medium or the concentration of the carbodiimide derivative, and therefore, use of the carbodiimide derivative is relatively restricted. Namely, if removal of the precipitate included in pores of the membrane is incomplete, the dialysis performance is reduced, and when the membrane is used as an artificial organ, there is a risk of an incorporation of the precipitate into the blood. On the other hand, in the case of carboxylic anhydride, for which a carbodiimide derivative need not be used, the above restriction does not apply.

The reaction medium used must not react with the organic carboxylic acid or the functional derivative thereof, must not deactivate the esterification catalyst, and must not cause a great morphological change in the polymeric membrane composed of the regenerated cellulose. Accordingly, all solvents satisfying these requirements and capable of dissolving or dispersing therein the organic carboxylic acid or the functional derivative thereof and the esterification catalyst can be used as the reaction medium. From the viewpoint of reaction uniformity, the reaction smoothness and the ease of removal of the catalyst or the like, use of a solvent capable of dissolving therein the organic carboxylic acid or the functional derivative thereof and the esterification catalyst is preferred. As examples of this preferred reaction medium, there can be mentioned hydrocarbons such as n-hexane, n-heptane, cyclohexane, petroleum ether, petroleum benzene, benzene, and toluene; ketones such as acetone and methyl ethyl ketone; esters such as methyl acetate, and ethyl acetate; ethers such as propyl ethyl ether, isopropyl ether, and dioxane; and chlorofluorinated hydrocarbons such as 1,1,2-trichloro-1,2,2-trifluoroethane, trichlorofluoromethane, and 1,1,2,2-tetrachloro-1,2-difluoroethane. These reaction media can be used singly or in the form of a mixture of two or more thereof. From the viewpoint of safety, and the ease of removal of the catalyst or the like after the reaction, a reaction medium containing a chlorofluorinated hydrocarbon, especially 1,1,2-trichloro-1,2,2-trifluoroethane, is preferable, and a mixed solvent of 1,1,2-trichloro-1,2,2-trifluoroethane with acetone is more preferable.

Various methods can be adopted for treating the regenerated cellulose. For example, a method can be adopted in which the regenerated cellulose membrane is immersed and stirred in a treating liquid prepared by dissolving or dispersing the organic carboxylic acid or the functional derivative thereof and the esterification catalyst in the reaction medium; a method in which the regenerated cellulose membrane is immersed in a tank filled with the treating liquid; and a method in which the treating liquid is circulated in a treating tube filled with the regenerated cellulose membrane. Furthermore, of course, a method can be adopted in which a dialyzer is set up by the regenerated cellulose membrane, and the treating liquid is constantly circulated or filled at least into the blood-contacting side of the dialyzer After termination of the esterification reaction, the regenerated cellulose membrane is separated from the treating liquid. Where no reactant, esterification catalyst or reaction by-product remains, washing is omitted, but ordinarily, washing is carried out to remove any remaining reactant, esterification catalyst or reaction by-product. This washing can be accomplished by an immersion extraction or Soxhlet extraction using the solvent used for the reaction or a solvent not causing a great morphological change in the membrane, such as methyl alcohol or ethyl alcohol. Finally, the residual solvent is removed by drying under a reduced pressure, air drying,or the like.

In the polymeric membrane composed of the regenerated cellulose, the surface of which has been thus esterified, the activation of the complement and the transient reduction of leukocytes are moderated without lowering the excellent dialysis performances of the polymeric membrane, as illustrated in the examples given hereinafter. It is considered that this effect probably occurs in the present invention, because the esterification reaction occurs only on the surface of the membrane and the chemical and physical structures are retained in the interior of the membrane. Furthermore, it is considered that the quantity of the functional group esterified to the membrane surface is sufficient to modify the physicochemical and biochemical properties of the membrane surface, but is small enough to ensure that adverse influences are not imposed on the permeation of water and of substances.

Therefore, according to the present invention, as pointed out hereinbefore, even though the carboxylic acid or the functional derivative thereof to be ester-bonded to the membrane surface is used at a low concentration, the regenerated cellulose is sufficiently modified. This effect could not be expected from the conventional technique. Namely, in the examples of European Patent No. 155,534 involving the reaction of a regenerated cellulose with an isocyanate prepolymer, the concentration of the reactant is considerably high at 1 to 15% by volume. On the other hand, according to the present invention, a satisfactory effect is attained at a concentration as low as several hundred ppm. The low-concentration operation is advantageous from the viewpoint of costs, and the maintaining of only a small amount of the residual reactant adhering to the membrane and washing of the membrane after the reaction are easily accomplished. Moreover, the low-concentration operation is advantageous from the viewpoint of safety during use.

Enhancement of the blood compatibility can be mentioned as another effect obtained by the modification of the physicochemical and biochemical properties of the membrane surface. Namely, if the grafted chain is hydrophilic, adsorption of a plasma protein is moderated. A theoretical basis for this phenomenon is found in Y. Ikada's Advances in Polymer Science, volume 57 (1984), page 103 onward. In brief, Ikada shows that, in a blood-containing surface having a hydrophilic chain grafted thereon, this grafted chain containing a large quantity of water suppresses an adsorption of proteins or adhesion of cells such as platelets to a substantial portion of the surface of the material, and accordingly, neither an adhesion of platelets to the blood-contacting surface, nor an activation of these platelets, nor a contact activation of blood coagulation occurs to any significant degree. Namely, it is considered that, in a blood-contacting surface where the adsorption of proteins is thus moderated, and the thrombus formation is suppressed.

On the other hand, where the grafted chain is hydrophobic, albumin is selectively adsorbed among plasma proteins. It is thought that albumin acts as a carrier for a fatty acid in blood and has a hydrophobic pocket at the center of the molecular axis, and it is considered that, since the hydrophobic grafted chain is bonded to this pocket, a selective adsorption takes place. Moreover, it is considered that, if the blood-contacting surface selectively absorbs albumin, almost no blood coagulation occurs. As the basis for this theory, it is considered that, although a protein having a saccharide chain, such as fibrinogen or immunoglobulin, is bonded to a platelet through this saccharide chain, albumin does not possess such a saccharide chain and does not cause specific bonding to a platelet, and therefore, blood coagulation does not occur to any significant degree in a blood-contacting surface preferentially adsorbing albumin.

For a control of the adsorption of proteins and an enhancement of the selective adsorption of albumin, the state where one end of the grafted chain is bonded to the surface of the polymeric membrane but the other end can move freely is preferable to the state where the grafted chain is bonded to the surface of the polymeric member at two or more points and the movement of the chain is inhibited. This is because the free grafted chain shields a substantial portion of the surface of the polymeric membrane and controls the adsorption of proteins. In the case of the hydrophilic grafted chain, an effect of an increase in the water content is manifested.

The membrane must be sterilized before use in a clinical treatment, and various sterilization methods can be utilized for the regenerated cellulose membrane of the present invention. Namely, a dialyzer in which the regenerated cellulose membrane is built is sterilized in the dry state, and an ethylene oxide gas sterilization, high pressure steam sterilization, and gamma ray sterilization can be utilized. Alternatively, sterilization is carried out in the state where the dialyzer in which the membrane is built is filled with water or a physiological saline solution, and then a high pressure steam sterilization and a gamma ray sterilization can be adopted.

The present invention will now be described in detail with reference to the following examples.

The measurements described in the examples were determined according to the following methods.

(1) Water permeability

A module was fabricated by fixing both ends of a bundle of 100 hollow fibers by an adhesive, and after water was filled in the interiors of the fibers, one end was closed and water was introduced under a pressure of 200 mmHg from the opening of the other end. The amount of permeating water per unit hour was measured. The membrane area of the hollow fibers was calculated from the measured values of the inner diameter of the fibers and the effective length of the module.

(2) Clearance

A module was fabricated in the same manner as described in (1) above, and an aqueous solution containing 1,000 ppm of urea or an aqueous solution containing 100 ppm of vitamin B-12 ($VB_{12}$) was used instead of water. The concentration in the dialyzate was determined from the absorbance measured by a spectrophotometer. The clearance was calculated according to the following formula:

$$\text{Clearance} = \frac{(\text{concentration in dialyzate}) \times (\text{amount of dialyzate per minute})}{(\text{concentration before dialysis})}$$

(3) Complement consumption ratio

A hollow fiber sample was cut to a size of 2 mm or a film sample was cut into a piece 2.5 mm × 2.5 mm, and the sample was placed in a polyethylene tube. A guinea pig complement (supplied by Cordis laboratory) was diluted 4 times by a gelatin-veronal buffer and 200 μl of the dilution was filled into the tube. Incubation was carried out at 37° C. for 1 hour. The complement value was determined according to the Mayer modified method [M.N. Mayer, Experimental Immunochemistry, 2nd edition, page 133, published by C.C. Tomas in 1961. Namely, the 50% hemolysis value (CH50 value) of the complement was determined and the complement consumption ratio (% CH50) to the control was calculated.

(4) EIA (enzyme immunity assay) method

Rabbit plasma was filled in hollow fibers and incubation was carried out at 37° C. for 1 hour. The rabbit plasma was then squeezed out from the hollow fibers and washed several times with a PBS buffer. Peroxidase-labelled antibodies (supplied by Cabel) to albumin, immunoglobulin G (IgG), and fibrinogen were filled in the sample composed of the hollow fibers having the plasma adsorbed on the surface thereof, and an antigen-antibody reaction with the adsorbed protein was carried out. The hollow fibers were washed with the PBS buffer, cut to a size of 2 mm, and the cut pieces were charged in a polyethylene tube. Then, 3-(p-hydroxyphenyl)propionic acid, which is a substrate for the oxidase, and hydrogen peroxide were added into the polyethylene tube to conduct an enzyme reaction for 1 hour. The formed oxide was measured by fluorometry.

(5) Adsorption amount of protein

Bovine serum albumin was radio-labelled with $^{125}I$ and an aqueous solution of the bovine serum albumin (bovine serum albumin concentration=0.3 mg/ml) was prepared. The sample was immersed in the aqueous solution at 37° C. for 3 hours. The unadsorbed protein was then removed by washing, and the radioactivity of the sample was measured, whereby the amount of the adsorbed protein was determined.

(6) Contact angle

A small drop of water was placed on the film sample, and the contact angle was measured at 25° C. by using a microscope.

EXAMPLE 1

A flask having an inner volume of 500 ml was charged with 0.25 g of polyethylene glycol dicarboxylic acid having an average molecular weight of 400 in the polyethylene glycol portion, 0.04 g of 4-dimethylaminopyridine, and 350 ml of benzene, and the mixture was stirred to prepare a solution. The solution was cooled to 10° C., and 100 regenerated cellulose hollow fiber membranes (inner diameter=200 μm, membrane wall thickness=11 μm, length=about 15 cm) were placed in the solution. After 10 minutes, the temperature was elevated to 30° C. and a reaction was carried out at this temperature for 15, 30, 60, 180, or 300 minutes, and 20 hollow fiber membranes were sampled at each time. The samples were subjected to immersion washing with the solvent used for the reaction and with methyl alcohol. The samples were then immersed in methyl alcohol for one day and night, and were then dried at room temperature under a reduced pressure to obtain modified hollow fiber membranes.

EXAMPLE 2

Modified hollow fiber membranes were prepared in the same manner as described in Example 1 except that 1.65 g of polyethylene glycol dicarboxylic acid having an average molecular weight of 980 in the polyethylene glycol portion, 0.40 g of dicyclohexylcarbodiimide, and 350 ml of benzene were used.

EXAMPLE 3

Modified hollow fiber membranes were prepared in the same manner as described in Example 1 except that 0.23 g of polyethylene glycol dicarboxylic acid having an average molecular weight of 400 in the polyethylene glycol portion, 0.01 g of 4-dimethylaminopyridine, 0.13 g of dicyclohexylcarbodiimide, and 350 ml of toluene were used, and the reaction temperature was changed to 35° C.

EXAMPLE 4

Modified hollow fiber membranes were prepared in the same manner as described in Example 1 except that 0.22 g of polyethylene glycol dicarboxylic acid having an average molecular weight of 400 in the polyethylene glycol portion, 0.02 g of 4-pyrrolidinopyridine, 0.15 g of dicyclohexylcarbodiimide, and 350 ml of ethyl acetate were used, and the reaction was carried out for 5, 10, 15, 20 or 30 minutes.

EXAMPLE 5

Modified hollow fiber membranes were prepared in the same manner as described in Example 1 except that 1.65 g of polyethylene glycol dicarboxylic acid having an average molecular weight of 980 in the polyethylene glycol portion, 0.01 g of 4-dimethylaminopyridine, 0.39 g of dicyclohexylcarbodiimide, and 350 ml of toluene were used.

EXAMPLE 6

Modified hollow fiber membranes were prepared in the same manner as described in Example 1 except that 6.12 g of polyethylene glycol dicarboxylic acid having an average molecular weight of 3,700 in the polyethylene glycol portion, 0.02 g of 4-dimethylaminopyridine, 0.14 g of dicyclohexylcarbodiimide, and 350 ml of toluene were used.

EXAMPLE 7

Modified hollow fiber membranes were prepared in the same manner as described in Example 1 except that 13.24 g of polyethylene glycol dicarboxylic acid having an average molecular weight of 7,800 in the polyethylene glycol portion, 0.03 g of 4-dimethylaminopyridine, 0.38 g of dicyclohexylcarbodiimide, and 350 ml of toluene were used.

EXAMPLE 8

A flask having an inner volume of 500 ml was charged with 34.10 g of polyethylene glycol dicarboxylic acid having an average molecular weight of 3,700 in the polyethylene glycol portion, 0.04 g of 4-dimethylaminopyridine, 2.58 g of dicyclohexylcarbodiimide, and 300 ml of toluene, and the mixture was stirred to prepare a solution. The solution was cooled to 10° C. and 8 cellulose films (thickness=17 μm, size=5 cm × 10 cm, average weight=0.04 g) were placed in the solution. After 10 minutes, the temperature was elevated to 30° C. and the reaction was carried out at this temperature for 15, 30, 60, 180 or 300 minutes. Samples were collected at each time and were subjected to immersion washing with the solvent used for the reaction and with methyl alcohol. The samples were immersed in methyl alcohol for one day and night, and then dried at room temperature under a reduced pressure to obtain modified cellulose membranes.

EXAMPLE 9

Modified cellulose membranes were prepared in the same manner as described in Example 8 except that 9.94 g of polyethylene glycol dicarboxylic acid having an average molecular weight of 3,700 in the polyethylene glycol portion, 0.09 g of p-toluenesulfonic acid and 300 ml of toluene were used, and 4 films were reacted at 50° C. for 30, 60, 180 or 300 minutes.

EXAMPLE 10

Modified cellulose membranes were prepared in the same manner as described in Example 8 except that 0.45 g of polyethylene glycol dicarboxylic acid having an average molecular weight of 400 in the polyethylene glycol portion, 0.004 g of 4-dimethylaminopyridine, 0.26 g of dicyclohexylcarbodiimide, and 300 ml of toluene were used, and one film was reacted at 50° C. for 300 minutes.

EXAMPLE 11

Modified cellulose membranes were prepared in the same manner as described in Example 8 except that 1.67 g of polyethylene glycol dicarboxylic acid having an average molecular weight of 3,700 in the polyethylene glycol portion, 57 ml of pyridine, and 43 ml of toluene were used, and one film was reacted at 80° C. for 300 minutes.

EXAMPLE 12

Modified hollow fiber membranes were prepared in the same manner as described in Example 1 except that 0.27 g of a chloride of polyethylene glycol dicarboxylic acid having an average molecular weight of 400 in the polyethylene glycol portion, 0.02 g of 4-dimethylaminopyridine, 1 ml of pyridine, and 350 ml of toluene were used, and the reaction was carried out for 10, 20, 30, 60 or 180 minutes.

EXAMPLE 13

Modified hollow fiber membranes were prepared in the same manner as described in Example 12 except that 0.63 g of a chloride of polyethylene glycol dicarboxylic acid having an average molecular weight of 980 in the polyethylene glycol portion, 0.01 g of 4-dimethylaminopyridine, 1 ml of pyridine, and 350 ml of toluene were used.

EXAMPLE 14

Modified hollow fiber membranes were prepared in the same manner as described in Example 12 except that 0.27 g of a chloride of polyethylene glycol dicarboxylic acid having an average molecular weight of 400 in the polyethylene glycol portion, 150 ml of pyridine, and 200 ml of toluene were used, and the reaction was carried out at 35° C.

EXAMPLE 15

Modified hollow fiber membranes were prepared in the same manner as described in Example 1 except that 0.10 g of methoxypolyethylene glycol carboxylic acid having an average molecular weight of 106 in the polyethylene glycol portion, 0.01 g of 4-dimethylaminopyridine, 0.13 g of dicyclohexylcarbodiimide, and 350 ml of toluene were used, and the reaction was carried out at 35° C.

EXAMPLE 16

Modified hollow fiber membranes were prepared in the same manner as described in Example 1 except that 0.20 g of ethoxypolyethylene glycol carboxylic acid having an average molecular weight of 106 in the polyethylene glycol portion, 0.02 g of 4-dimethylaminopyridine, 0.26 g of dicyclohexylcarbodiimide, and 350 ml of ethyl acetate were used, and the reaction was carried out at 50° C.

EXAMPLE 17

Modified hollow fiber membranes were prepared in the same manner as described in Example 1 except that 0.26 g of a chloride of methoxypolyethylene glycol carboxylic acid having an average molecular weight of 106 in the polyethylene glycol portion, 0.05 g of 4-pyrrolidinopyridine, 2 ml of pyridine, and 350 ml of toluene were used, and the reaction was carried out at 40° C. for 10, 20, 30, 60 or 180 minutes.

EXAMPLE 18

Modified hollow fiber membranes were prepared in the same manner as described in Example 17 except that 0.36 g of a chloride of ethoxypolyethylene glycol carboxylic acid having an average molecular weight of 106 in the polyethylene glycol portion, 0.03 g of 4-pyrrolidinopyridine, 2 ml of pyridine, and 350 ml of toluene were used.

EXAMPLE 19

The complement consumption ratio for each of the modified hollow fiber membranes and modified cellulose membranes obtained in Examples 1 through 18, was determined, and the results are shown in Table 1.

TABLE 1

| Reaction time (min) | Complement Consumption Ratio (% CH50) | | | | | | | | |
|---|---|---|---|---|---|---|---|---|---|
| | 0 | 5 | 10 | 15 | 20 | 30 | 60 | 180 | 300 |
| Example 1 | 41 | — | — | 34 | — | 27 | 23 | 20 | 21 |
| Example 2 | 58 | — | — | 41 | — | 33 | 29 | 27 | 28 |
| Example 3 | 40 | — | — | 10 | — | 10 | 5 | 7 | 8 |
| Example 4 | 40 | 29 | 21 | 30 | 12 | 15 | — | — | — |
| Example 5 | 53 | — | — | 38 | — | 32 | 25 | 22 | 26 |
| Example 6 | 47 | — | — | 33 | — | 31 | 27 | 30 | 25 |
| Example 7 | 55 | — | — | 51 | — | 49 | 48 | 33 | 30 |
| Example 8 | 47 | — | — | 35 | — | 31 | 31 | 29 | 31 |
| Example 9 | 45 | — | — | — | — | 20 | 21 | 14 | 11 |
| Example 10 | — | — | — | — | — | — | — | — | 8 |
| Example 11 | — | — | — | — | — | — | — | — | 13 |
| Example 12 | 41 | — | 27 | — | 25 | 26 | 24 | 25 | — |
| Example 13 | 43 | — | 33 | — | 36 | 35 | 28 | 30 | — |
| Example 14 | 41 | — | 25 | — | 27 | 24 | 25 | 27 | — |
| Example 15 | 54 | — | — | 39 | — | 37 | 37 | 40 | 42 |
| Example 16 | 39 | — | — | 38 | — | 32 | 32 | 32 | 40 |
| Example 17 | 47 | — | 38 | — | 39 | 40 | 40 | 42 | — |
| Example 18 | 41 | — | 19 | — | 20 | 20 | 22 | 21 | — |

EXAMPLE 20

Esterification reaction was carried out under the same conditions as described in Example 3, and samples were collected when the reaction was conducted for 15, 60, 120, 180, 240 and 300 minutes. The amount of the adsorbed protein was measured for each of the samples, and the results are shown in Table 2.

EXAMPLE 21

Esterification reaction was carried out under the same conditions as described in Example 10, and cellulose film samples were collected when the reaction was conducted for 15, 30, 60, 120, 180, 240 and 300 minutes. The contact angle was measured for each of the obtained samples, and the results are shown in Table 2.

TABLE 2

Protein Adsorption and Contact Angle

| Reaction time (min) | Amount of adsorbed serum albumin ($\mu g/cm^2$) | Contact angle (degree) |
| --- | --- | --- |
| 0 | 0.30 | 24 |
| 15 | 0.15 | 20 |
| 30 | — | 27 |
| 60 | 0.19 | 17 |
| 120 | 0.14 | 28 |
| 180 | 0.17 | 21 |
| 240 | 0.12 | 27 |
| 300 | 0.15 | 25 |

EXAMPLE 22

A bundle of about 7,000 regenerated cellulose hollow fiber membranes (inner diameter = 200 μm, membrane wall thickness = 13 μm, length = 30 cm) was filled in a stainless steel tube having nozzles at upper and lower ends thereof. Separately, a flask having an inner volume of 1,000 ml was charged with 2.47 g of polyethylene glycol dicarboxylic acid having an average molecular weight of 400 in the polyethylene glycol portion, 0.15 g of 4-dimethylaminopyridine, 1.01 g of dicyclohexylcarbodiimide, and 700 ml of a 1,1,2,3-trichloro-1,2,2-trifluoroethane/acetone mixed solvent (the acetone content was 12.5% by weight), to prepare a treating liquid. The treating liquid was introduced into the stainless tube from the lower nozzle by using a tube pump while the effluent from the upper nozzle was returned to the flask. The treating liquid was circulated in this manner for 30 minutes, and the stainless steel tube and flask were placed in a water bath so that the temperature of the treating liquid was maintained at 35° C.

The treated hollow fiber membrane bundle was then immersed in methyl alcohol for one day and night and dried at room temperature under a reduced pressure to obtain a modified hollow fiber membrane bundle.

The dialysis performance and complement consumption ratio for the hollow fiber membrane bundle subjected to the above-mentioned esterification treatment, and the untreated hollow fiber membrane bundle, were measured, and the results are shown in Table 3.

TABLE 3

| | Esterified Sample | Untreated Sample |
| --- | --- | --- |
| Water permeability ($ml/m^2 \cdot mmHg \cdot hr$) | 4.7 | 4.7 |
| Urea clearance (ml/min) | 172 | 170 |
| $VB_{12}$ clearance (ml/min) | 51 | 49 |
| Complement consumption ratio (% CH50) | 12 | 48 |

EXAMPLE 23

In Example 22, the treating liquid after completion of the reaction was opaque because of the presence of a precipitate. In order to examine influences of this precipitate, the esterification was carried out in the same manner as described in Example 22, the obtained hollow fiber membrane bundle was washed only with the reaction medium and dried at room temperature under a reduced pressure, and the water permeability was measured. The hollow fiber membranes were cut to a length of 2 to 3 mm and subjected to Soxhlet extraction (12 hours) by using methyl alcohol to extract dicyclohexylurea. This dicyclohexylurea was determined by gas chromatography. The results are shown in Table 4.

EXAMPLE 24

To 750 ml of a 1,1,2-trichloro-1,2,2-trifluoroethane/acetone mixed solvent (the acetone content was 12.5% by weight) were added 2.47 g of polyethylene glycol dicarboxylic acid having an average molecular weight of 400 in the polyethylene glycol portion and 1.01 g of dicyclohexylcarbodiimide, and the mixture was stirred at room temperature for 30 minutes. The formed precipitate of dicyclohexylurea was separated by filtration, the obtained polyethylene glycol dicarboxylic acid filtrate was transferred to a flask having a volume of 1,000 ml, and 0.15 g of 4-dimethylaminopyridine was added to the filtrate to prepare a treating liquid. Using this treating liquid, the esterification treatment was carried out in the same manner as described in Example 22, the obtained hollow fiber membrane bundle was washed and dried in the same manner as described in Example 23, and the water permeability and the amount of adhering dicyclohexylurea were measured. The results are shown in Table 4.

The complement consumption ratio of the esterified hollow fiber membrane was measured, and it was found that the complement consumption ratio was 16%.

TABLE 4

| | Example 23 | Example 24 |
| --- | --- | --- |
| Water permeability (% based on that of untreated hollow fibers) | 82 | 102 |
| Amount of dicyclohexylurea (mg/g of hollow fibers) | 40 | Not detected |

EXAMPLE 25

To 250 ml of a 1,1,2-trichloro-1,2,2-trifluoroethane/acetone mixed solvent (the acetone content was 12.5% by weight) were added 0.25 g of an alkoxypolyethylene glycol monocarboxylic acid $[C_{13}H_{27}-(OCH_2CH_2-)_7-OCH_2CO_2H]$, 0.01 g of 4-diemthylaminopyridine, and 0.09 g of dicyclohexylcarbodiimide, to prepare a treating liquid. Then, about 600 regenerated cellulose hollow fiber membranes (inner diameter = 200 μm, wall thickness = 13 μm, length = about 20 cm) were vertically immersed in this treating liquid for 2 hours and were occasionally moved vertically up and down. The treated hollow fiber membranes were then immersed in methyl alcohol for one day and night and dried at room temperature under a reduced pressure to obtain regenerated cellulose hollow fiber membranes. The complement consumption ratio was found to be 11%.

EXAMPLE 26

To 250 ml of a 1,1,2-trichloro-1,2,2-trifluoroethane/acetone mixed solvent (the acetone content was 12.5%) were added 0.047 g of caproic acid, 0.01 g of 4-dimethylaminopyridine, and 0.09 g of dicyclohexylcarbodiimide, to prepare a treating liquid. About 600 regenerated cellulose hollow fiber membranes (inner diameter = 200 μm, wall thickness = 13 μm, length × about 20 cm) were vertically immersed in the treating liquid for 2 hours and were occasionally moved vertically up and down. The treated hollow fiber membranes were then immersed in methyl alcohol for one day and night and dried at room temperature under a reduced pressure to obtain regenerated cellulose hollow fiber membranes. The results of the measurement of the complement consumption ratio are shown in Table 5.

EXAMPLE 27

Esterification was carried out in the same manner as described in Example 26 except that aliphatic carboxylic acid (saturated fatty acids, unsaturated fatty acids and aliphatic dicarboxylic acids) shown in Table 3 were used instead of caproic acid. The amounts of the aliphatic carboxylic acids used and the complement consumption ratios of the esterified regenerated cellulose hollow fiber membranes are shown in Table 5.

TABLE 5

| Aliphatic Carboxylic Acid | Amount (mg) | Complement Consumption Ratio (%) |
|---|---|---|
| Caproic acid | 47 | 13 |
| Capric acid | 70 | 13 |
| Lauric acid | 81 | 15 |
| Myristic acid | 93 | 16 |
| Palmitic acid | 104 | 15 |
| Stearic acid | 115 | 11 |
| Arachic acid | 127 | 10 |
| Behenic acid | 138 | 15 |
| Oleic acid | 115 | 12 |
| Linoleic acid | 114 | 12 |
| Linolenic acid | 113 | 13 |
| Adipic acid | 59 | 18 |
| Sebacic acid | 82 | 17 |

EXAMPLE 28

To 250 ml of a 1,1,2-trichloro-1,2,2-trifluoroethane/acetone mixed solvent (the acetone content was 12.5% by weight) were added 0.047 g caproic anhydride and 0.01 g 4-dimethylaminopyridine, to prepare a treating liquid. Using this treating liquid, regenerated cellulose hollow fiber membranes were treated in the same manner as described in Example 26. The complement consumption ratio of the obtained hollow fiber membranes is shown in Table 6.

EXAMPLE 29

Esterification was carried out in the same manner as described in Example 28 except that aliphatic carboxylic anhydrides shown in Table 6 were used instead of caproic anhydride. The amounts of the aliphatic carboxylic acid anhydrides used and the complement consumption ratios of the esterified regenerated cellulose hollow fiber membranes are shown in Table 6.

TABLE 6

| Aliphatic Carboxylic Anhydride | Amount (mg) | Complement Consumption Ratio (%) |
|---|---|---|
| Caproic anhydride | 43 | 13 |
| Caprylic anhydride | 55 | 13 |
| Capric anhydride | 66 | 15 |
| Lauric anhydride | 78 | 16 |

EXAMPLE 30

An EIA measurement was carried out for each of the regenerated cellulose hollow fiber membranes obtained in Examples 26 through 29, and the results are shown in Table 7. More specifically, the fluorescence intensities Ia, Ii and If were determined by using an anti-alubumin antibody, anti-immunoglobulin G antibody, and anti-fibrinogen antibody, respectively, the values Ia/Ii and Ia/If were determined, and the values (Alb/IgG) and (Alb/Fib) were calculated by dividing these values Ia/Ii and Ia/If by those of the untreated hollow fiber membrane. Each of the so obtained values was larger than 1.00, and it was confirmed that these modified hollow fiber membranes selectively adsorbed albumin in larger amounts, than the untreated hollow fiber membrane.

TABLE 7

| Aliphatic Carboxylic Acid | (Alb/IgG) | (Alb/Fib) |
|---|---|---|
| Caproic acid | 1.14 | 1.38 |
| Lauric acid | 1.02 | 1.37 |
| Myristic acid | 1.35 | 1.09 |
| Palmitic acid | 1.61 | 1.34 |
| Stearic acid | 3.23 | 3.55 |
| Arachic acid | 2.82 | 1.50 |
| Behenic acid | 1.99 | 2.01 |
| Oleic acid | 3.36 | 2.06 |
| Linoleic acid | 1.14 | 1.37 |
| Linolenic acid | 1.27 | 1.62 |
| Caprylic anhydride | 1.40 | 1.34 |
| Capric anhydride | 1.33 | 1.44 |
| Lauric anhydride | 1.25 | 1.53 |

EXAMPLE 31

A treating liquid was prepared by adding 0.44 g of caprylic acid, 0.02 g of 4-dimethylaminopyridine, and 0.26 g of dicyclohexylcarbodiimide to 700 ml of a 1,1,2-trichloro-1,2,2-trifluoroethane/acetone mixed solvent (the acetone content was 12.5% by weight). A bundle of about 7,000 regenerated cellulose hollow fiber membranes (inner diameter=200 μm, membrane wall thickness=13 μm, length=30 cm) was vertically immersed in the treating liquid for 30 minutes and were occasionally moved vertically up and down. The bundle was then immersed in methyl alcohol for one day and night and dried at room temperature under a reduced pressure to obtain an esterified hollow fiber membrane bundle.

The results of a measurement of the dialysis performance and complement consumption ratio of the esterified hollow fiber membranes are shown in Table 8.

EXAMPLE 32

The esterification treatment was carried out in the same manner as described in Example 31 except that a treating liquid obtained by adding 0.44 g of caproic anhydride and 0.02 g of dimethylaminopyridine to 700 ml of a 1,1,2-trichloro-1,2,2-trifluoroethane/acetone mixed solvent (the acetone content was 12.5% by weight) was used.

The dialysis performance and complement consumption ratio of the obtained hollow fiber membranes are shown in Table 8.

TABLE 8

| | Example 31 | Example 32 |
|---|---|---|
| Water permeability (ml/m$^2$ · mmHg · hr) | 4.0 | 3.9 |
| Urea clearance (ml/min) | 162 | 159 |
| VB$_{12}$ clearance (ml/min) | 44 | 44 |
| Complement consumption ratio (%) | 13 | 12 |

EXAMPLE 33

The treated regenerated cellulose hollow fiber membranes obtained in Examples 22, 31 and 32 and the untreated regenerated cellulose membranes were built into dialyzers, and the extracorporeal circulation test was carried out by using a beagle dog having a body weight of about 10 kg. Blood was taken at a rate of 100 ml/min from a shunt formed in the neck of the dog and introduced into the blood side of the dialyzer. Before the extracorporeal circulation, the interior of the dialyzer was washed with a physiological saline solution and the dialyzer and a blood passage were filled with a physiological saline solution containing 6,000 U/1 of heparin. Then, circulation of blood was started. Blood was sampled from the inlet portion of the dialyzer and the number of leulocytes was measured. Relative values obtained 15 and 30 minutes from the start of the dialysis, calculated based on the assumption that the number of leukocytes just after the start of the dialysis was 100, are shown in Table 9.

TABLE 9

| Hollow Fiber Membrane | Value after 15 Minutes | Value after 30 Minutes |
|---|---|---|
| Example 22 | 78 | 82 |
| Example 31 | 81 | 94 |
| Example 32 | 85 | 92 |
| Untreated | 13 | 45 |

EXAMPLE 34

A plugged Erlenmeyer flask having a volume of 200 ml was charged with 0.035 g of caproic anhydride, 0.004 g of 4-dimethylaminopyridine, and 100 ml of a 1,1,2-trichloro-1,2,2-trifluoroethane/acetone mixed solvent (the acetone content was 12.5% by weight), to prepare a treating liquid. The treating liquid was allowed to stand at room temperature for 2 hours, and 4.5 g of regenerated cellulose hollow fiber membranes (wall thickness=13 $\mu$m, inner diameter=200 $\mu$m) cut to a size of 2 to 3 mm were placed in the treating liquid. The flask was closed by a plug and shaken for 30 minutes in a water bath at 30° C. Then, the hollow fiber membranes were taken out and immersed in methyl alcohol for one day and night. The membranes were collected by filtration and dried at room temperature under a reduced pressure.

Similarly, hollow fiber membranes were obtained by using treating liquids allowed to stand at room temperature for 4, 6, 8 and 16 hours, respectively, after the preparation.

The results of the measurement of the complement consumption ratio are shown in Table 10. It was confirmed that the reactivity of the treating liquid was not changed by 16 hours' standing and improvements similar to those attained by the treating liquid after 2 hours' standing were attained.

EXAMPLE 35

A plugged Erlenmyer flask having a volume of 200 ml was charged with 0.065 g of polyethylene glycol dicarboxylic acid having an average molecular weight of 400 in the polyethylene glycol portion, 0.004 g of 4-dimethylaminopyridine, 0.037 g of dicyclohexylcarbodiimi, and 100 ml of a 1,1,2-trichloro-1,2,2trifluoro-/acetone mixed solvent (the acetone content was 12.5% by weight), to prepare a treating liquid. The treatment was carried out in the same manner as in Example 34 except that the standing time was adjusted to 0.5, 1, 2, 4, 6 and 8 hours.

The results of the measurement of the complement consumption ratio are shown in Table 10. It was found that if the standing time was longer than 2 hours, the reactivity was reduced.

TABLE 10

| Standing Time (hours) | Example 34 | Example 35 |
|---|---|---|
| 0.5 | — | 15% |
| 1 | — | 13% |
| 2 | 14% | 26% |
| 4 | 14% | 35% |
| 6 | 12% | 47% |
| 8 | 13% | 50% |
| 16 | 14% | — |

The following prominent effects can be attained according to the present invention.

(a) As shown in Tables 1, 5 and 6, activation of the complement is controlled, and as shown in Example 33, a transient reduction of leukocytes can be drastically moderated.

(b) As shown in Table 2, the contact angle is not changed by the treatment and the physical and chemical properties can be retained, and as shown in Tables 3 and 8, the water permeation performance and the permeability of the membrane are approximately the same as those of the untreated cellulose membrane.

(c) As shown in Tables 2 and 7, an effect of modifying the biological properties of the surface is attained. Namely, if a hydrophilic grafted chain is bonded to the surface, the amount of proteins adsorbed is reduced, and if a hydrophobic grafted chain is bonded to the surface, the selective adsorption of albumin is increased. In each case, the thrombus formation is suppressed and the blood compatibility of the membrane is improved.

(d) The temperature required for the preparation is low and the reaction time is short, and for this reason also, the physical properties of the membranes are not changed.

(e) The membrane can be easily prepared and the used reactants can be easily removed. Therefore, according to the present invention, a dialysis membrane having a high safety level can be obtained economically advantageously.

We claim:

1. An improved regenerated cellulose membrane characterized in that said membrane is formed by ester-bonding an organic carboxylic acid or a functional derivative thereof to at least a blood-contacting surface of a polymeric membrane comprising a regenerated cellulose; said organic carboxylic acid being at least one member selected from the group consisting of organic monocarboxylic acids and polyethylene glycol dicarboxylic acids.

2. An improved regenerated cellulose membrane as set forth in claim 1, wherein the organic carboxylic acid has at least 5 carbon atoms.

3. An improved regenerated cellulose membrane as set forth in claim 1, wherein the organic carboxylic acid derivative is an organic carboxylic anhydride.

4. An improved regenerated cellulose membrane as set forth in claim 1, wherein the organic monocarboxylic acid is a saturated or unsaturated fatty acid having 5 to 30 carbon atoms.

5. An improved regenerated cellulose membrane as set forth in claim 1, wherein the organic monocarboxylic acid represented by the following formula:

$$HO_2CCH_2-(OCH_2CH_2)_n-OR$$

wherein R stands for a saturated or unsaturated hydrocarbon group having 1 to 20 carbon atoms and n is an integer of from 1 to 150.

6. An improved regenerated cellulose membrane as set forth in claim 1, wherein the a polyethylene glycol dicarboxylic acid is represented by the following formula:

7. A process for the preparation of an improved regenerated cellulose membrane, which comprises treating at least a blood-contacting surface of a polymeric membrane comprising a regenerated cellulose with a liquid prepared by dissolving or dispersing an organic carboxylic acid or a functional derivative thereof and an esterification catalyst in a reaction medium to effect esterification reaction between the organic carboxylic acid or the functional derivative thereof and the hydroxyl groups on the surface of the membrane; said organic carboxylic acid being at least one member selected from the group consisting of organic monocarboxylic acids and polyethylene glycol dicarboxylic acids.

8. A process for the preparation of an improved regenerated cellulose membrane according to claim 7, wherein the esterification catalyst is soluble in the reaction medium.

9. A process for the preparation of an improved regenerated cellulose membrane according to claim 7, wherein the reaction medium is at least one member selected from the group consisting of hydrocarbons, ketones, esters, ethers and chlorofluorinated hydrocarbons.

10. A process for the preparation of an improved regenerated cellulose membrane according to claim 7, wherein the reaction medium is a mixed solvent of 1,1,2-trichloro-1,2,2-trifluoroethane with acetone.

* * * * *

UNITED STATES PATENT AND TRADEMARK OFFICE
CERTIFICATE OF CORRECTION

PATENT NO. : 4,999,110

DATED : March 12, 1991

INVENTOR(S) : IKADA et al.

It is certified that error appears in the above-identified patent and that said Letters Patent is hereby corrected as shown below:

Claim 6, line 4 (Col. 19, line 14): after "mula:" insert --$HO_2CCH_2-(OCH_2CH_2)_n-OCH_2CO_2H$ wherein $n$ is an integer of from 1 to 150.--

Signed and Sealed this

Eighteenth Day of August, 1992

Attest:

DOUGLAS B. COMER

*Attesting Officer*  *Acting Commissioner of Patents and Trademarks*